(12) United States Patent
Yamada et al.

(10) Patent No.: US 9,421,294 B2
(45) Date of Patent: Aug. 23, 2016

(54) DEODORIZING MASK

(71) Applicant: TOAGOSEI CO., LTD., Minato-ku (JP)

(72) Inventors: Yoshinao Yamada, Nagoya (JP); Koji Sugiura, Nagoya (JP)

(73) Assignee: TOAGOSEI CO., LTD., Minato-ku (JP)

( * ) Notice: Subject to any disclaimer, the term of this patent is extended or adjusted under 35 U.S.C. 154(b) by 0 days.

(21) Appl. No.: 14/382,950

(22) PCT Filed: Mar. 4, 2013

(86) PCT No.: PCT/JP2013/055789
§ 371 (c)(1),
(2) Date: Sep. 4, 2014

(87) PCT Pub. No.: WO2013/133195
PCT Pub. Date: Sep. 12, 2013

(65) Prior Publication Data
US 2015/0056102 A1 Feb. 26, 2015

(30) Foreign Application Priority Data

Mar. 7, 2012 (JP) .................................. 2012-049866

(51) Int. Cl.
*B01D 50/00* (2006.01)
*B01D 46/00* (2006.01)
(Continued)

(52) U.S. Cl.
CPC ................ *A61L 9/014* (2013.01); *B01D 39/16* (2013.01); *A41D 13/1115* (2013.01); *B01D 2239/045* (2013.01); *B01D 2239/065* (2013.01); *B01D 2239/0618* (2013.01)

(58) Field of Classification Search
CPC .......... A61L 2/022; A61L 9/014; A62D 9/00; A62B 18/00; C08L 666/02
USPC .................. 55/315, 482; 95/273, 901; 96/147
See application file for complete search history.

(56) References Cited

FOREIGN PATENT DOCUMENTS

| CN | 1651112 A | 8/2005 |
|---|---|---|
| CN | 201798054 U | 4/2011 |

(Continued)

OTHER PUBLICATIONS

International Search Report issued Apr. 2, 2013 in PCT/JP2013/055789.

(Continued)

*Primary Examiner* — Monzer R Chorbaji
(74) *Attorney, Agent, or Firm* — Oblon, McClelland, Maier & Neustadt, L.L.P.

(57) ABSTRACT

A deodorizing mask includes an air permeable mask main body for covering nose and mouth of the user with at least two types of nonwoven cloth, the mask main body having a deodorizing nonwoven cloth layer including a chemical adsorptive deodorizer and a dustproof nonwoven cloth layer having a dustproof effect, and the air permeability of the dustproof nonwoven cloth layer being ⅔ or less of the air permeability of the deodorizing nonwoven cloth layer. Preferably, the air permeability of the dustproof nonwoven cloth layer is in a range of 10 to 120 cm/(cm·s) in a permeated air quantity based on the Frazir method, the air permeability of the deodorizing nonwoven cloth layer is in a range of 40 to 400 cm/(cm·s) in a permeated air quantity based on the Frazir method, and the permeated air quantity of the dustproof nonwoven cloth layer is ⅔ or less of the permeated air quantity of the deodorizing nonwoven cloth layer.

19 Claims, 3 Drawing Sheets

(51) Int. Cl.
*B01D 53/02* (2006.01)
*A61L 9/014* (2006.01)
*B01D 39/16* (2006.01)
*A41D 13/11* (2006.01)

(56) References Cited

FOREIGN PATENT DOCUMENTS

| | | |
|---|---|---|
| CN | 102182062 | 9/2011 |
| EP | 2 484 409 A1 | 8/2012 |
| JP | 62-87174 A | 4/1987 |
| JP | 05-33743 U | 5/1993 |
| JP | 05-65354 U | 8/1993 |
| JP | 09-47500 A | 2/1997 |
| JP | 10-108915 A | 4/1998 |
| JP | 2000-279500 A | 10/2000 |
| JP | 2002-200149 A | 7/2002 |
| JP | 2005-152560 A | 6/2005 |
| JP | 2007-159796 A * | 6/2007 ............. A62B 23/02 |
| JP | 2008-295961 A | 12/2008 |
| JP | 2009-201634 A | 9/2009 |
| JP | 2009-221618 A | 10/2009 |
| JP | 2011-104274 A | 6/2011 |
| JP | 2011-125596 A | 6/2011 |
| TW | I264315 | 10/2006 |
| WO | WO 2011/040035 A | 4/2011 |

OTHER PUBLICATIONS

Combined Office Action and Search Report issued Oct. 10, 2015 in Chinese Patent Application No. 201380010102.5 (with English language translation).

Office Action in corresponding Taiwanese application No. 102107848, dated Mar. 22, 2016. (w/English Translation).

Office Action in corresponding Chinese application No. 201380010102.5, dated May 23, 2016. (w/English Translation).

\* cited by examiner

DEODORIZING MASK

FIELD OF THE INVENTION

The present invention relates to a deodorizing mask that exerts an outstanding deodorizing effect against offensive odors generated by excreta, putrescence, or the like.

BACKGROUND ART

Conventionally, masks of various kinds such as antibacterial masks, antiviral masks, antiallergic masks, and deodorizing masks have been disclosed. Among them are a particularly large number of deodorizing masks containing deodorizers: for example, a mask with an activated carbon sheet in its filter (see Patent Literature 1), a mask with an odor adsorption sheet made of a water-containing magnesium silicate clay mineral (see Patent Literature 2), and a deodorizing mask with an air-permeable material attached to its air-permeable portion wherein at least a metal selected from Fe, Mn, Al, Zn and Cu, and a reaction product of the metal and oxypolybasic acids coexist in the air-permeable material (see Patent Literature 3). However, adequate deodorizing effects are not expected from physisorption-type deodorizers, such as activated carbons. Besides, prolonged use of these deodorizers causes release of adsorbed malodorous gases. The water-containing magnesium silicate clay minerals, whose original deodorizing effects are not so high, cannot obtain satisfactory deodorizing effects unless these materials are abundantly used and sheet treatments are properly performed. As to the materials coexistently containing reaction products of the metals and the oxypolybasic acids but with no binder contained therein, it is difficult to use large quantities of these materials in the air-permeable portion. This may cause maldistribution of the deodorizer, diminishing its deodorizing effect. As is the case with the before-mentioned materials, an adequate deodorizing performance is not possible.

So far has been disclosed a three-dimensional deodorizing mask with a four-layer structure, wherein malodorous gases can be thoroughly absorbed by a nonwoven fabric with porous ceramic particles adhered thereto (see Patent Literature 4). More specifically describing the mask, porous ceramic particles are spread and adhered onto a polyester-based nonwoven fabric by means of an acrylic resin so that an ⅓ area of the ceramic particles is thereby covered, and a microfiber nonwoven fabric is further provided on the face side of the deodorizing nonwoven fabric as a collection layer. Any details of the deodorizing performance of this particular invention are unknown because types of used gases and duration of its deodorizing effect are not stated. This conventional example did not study the deodorizing effect of the whole mask but only confirmed the deodorizing ratio in the deodorizing test where the deodorizing nonwoven fabric alone was solely used, which was 96% by volume. This deodorizing ratio is extremely low for practical use. As is known from the Weber-Fechner's law, the human sense of odor is commonly poor. For example, reduction of a malodorous gas by 90% by volume can only be perceived as not more than 50% reduction. Therefore, one is never satisfied with the deodorizing effect unless the deodorizing ratio is, at the minimum, 99.9% or more by volume, or desirably, 99.99% or more by volume.

A deodorizing mask is proposed which includes, in its layers, a fabric, paper or chemical product having ion exchangeability targeted for ammonia-containing gases (see Patent Literature 5). With such a deodorizer characterized by ion exchangeability, which is a chemisorption-type deodorizer, a high deodorizing performance may be possible. This document, however, discloses neither specific components nor formulation of the deodorizer, failing to demonstrate whether the deodorizing effect of this mask meets the requirements of practicality or whether the production of such a mask is feasible.

Another example which has been disclosed is a three-dimensional mask formed in the shape of a bowl wherein a nonwoven fabric forming a mask body includes, by 30% to 50% by mass, a fiber carrying a metal complex having a redox ability and/or a fiber carrying metal ions (see Patent Literature 6). Such a deodorizer should be included in the category of chemisorption-type deodorizers, which may accomplish a high deodorizing performance depending on a method of use. Yet, the mask, if formed in a monolayer structure, often retains therein malodorous gases passing through. Again, the deodorizing effect of this mask is not very high.

In the meantime, chemisorption-type deodorizers have been developed, which are advantageous in that small quantities enable high deodorizing performances (see Patent Literatures 7, 8, and 9). Such chemisorption-type deodorizers capture odors through reactions, thereby effectively eliminating odors in short periods of time. However, offensive odors to be captured by masks are generated by gaseous matters, and contacts between the deodorizers and malodorous gases are instantaneous. As far as a nonwoven fabric carrying a deodorizer has an air permeability, there are certainly some malodorous gases passing through the nonwoven fabric without contacting the deodorizer. Thus far, deodorizing masks, which advantageously reduce any offensive odors to a hardly-perceivable level, are yet to be invented. On the other hand, consumers are increasingly demanding comfortableness when they are wearing the masks. They want a mask that causes no discomfort and accomplishes a high deodorizing performance by efficiently adsorbing malodorous gases.

PRIOR ART LITERATURE

Patent Literature

Patent Literature 1: Japanese Unexamined Patent Application Publication No. 2011-125596
Patent Literature 2: Japanese Unexamined Patent Application Publication No. Sho 62-87174
Patent Literature 3: Japanese Unexamined Patent Application Publication No. Hei 5-33743
Patent Literature 4: Japanese Unexamined Patent Application Publication No. 2007-159796
Patent Literature 5: Japanese Unexamined Patent Application Publication No. 2005-152560
Patent Literature 6: Japanese Unexamined Utility Model Application Publication No. Hei 5-65354
Patent Literature 7: Japanese Unexamined Patent Application Publication No. 2000-279500
Patent Literature 8: Japanese Unexamined Patent Application Publication No. 2002-200149
Patent Literature 9: Japanese Unexamined Patent Application Publication No. 2011-104274

SUMMARY OF THE INVENTION

Problems to be Solved by the Invention

An object of the present invention is to provide a deodorizing mask which exerts an outstanding deodorizing effect against offensive odors generated by excreta, putrescence, or the like.

Means for Solving the Problems

The present inventors earnestly worked on the conventional problems, and finally found out that the problems could be solved by the use of a deodorizing nonwoven fabric layer containing a chemisorption-type deodorizer in addition to a dust-proof nonwoven fabric layer, wherein the dust-proof nonwoven fabric layer with an air permeability inferior to that of the deodorizing nonwoven fabric layer is provided on the face side of a mask. More specifically, the present invention is a deodorizing mask that has a deodorizing nonwoven fabric layer containing a chemisorption-type deodorizer and a dust-proof nonwoven fabric layer having a dust-prevention effect, wherein the dust-proof nonwoven fabric layer has an air permeability equal to or smaller than ⅔ of that of the deodorizing nonwoven fabric layer.

The description of this invention uses the term "malodorous component" for any matter that is a source of malodor, and uses the term "malodorous gas" for any gases containing malodors.

In the present invention, it is particularly preferable to use a chemisorption-type deodorizer having a high reaction rate with malodorous components included in malodorous gases. Specifically, it is preferable to use a chemisorption-type deodorizer in which a quantity of malodorous component that can be deodorized by 0.1 g of the chemisorption-type deodorizer per minute is equal to or larger than a quantity of malodorous component included in 10 L of a malodorous gas at odor intensity grade 5 of a six grades odor intensity measurement method. The deodorizing nonwoven fabric layer preferably includes at least two different chemisorption-type deodorizers.

Effect of the Invention

The deodorizing mask of the present invention exerts an outstanding deodorizing effect against offensive odors generated by, for example, excreta or putrescence. Wearing the mask, therefore, diminishes a sense of discomfort in any sites where malodorous gases are wafting around.

The deodorizing mask of the present invention is advantageously used in, for example, sewage treatment plants, waste water treatment plants, livestock farms, garbage disposal plants, fertilizer plants, chemical plants, food-processing factories, fishery harbors, health care sites, nursing care sites where handling of excreta is required, sites where cleaning services are provided, zoos, restaurants, and lavatories. With the use of a chemisorption-type deodorizer having a high rate of reaction between malodorous components included in malodorous gases and respiratory air whose gas flow rate is instantaneously high, the mask advantageously achieves a very high deodorizing effect that offensive odors are hardly perceived immediately after the mask is put on.

DESCRIPTION OF THE EMBODIMENTS

Figure 1:
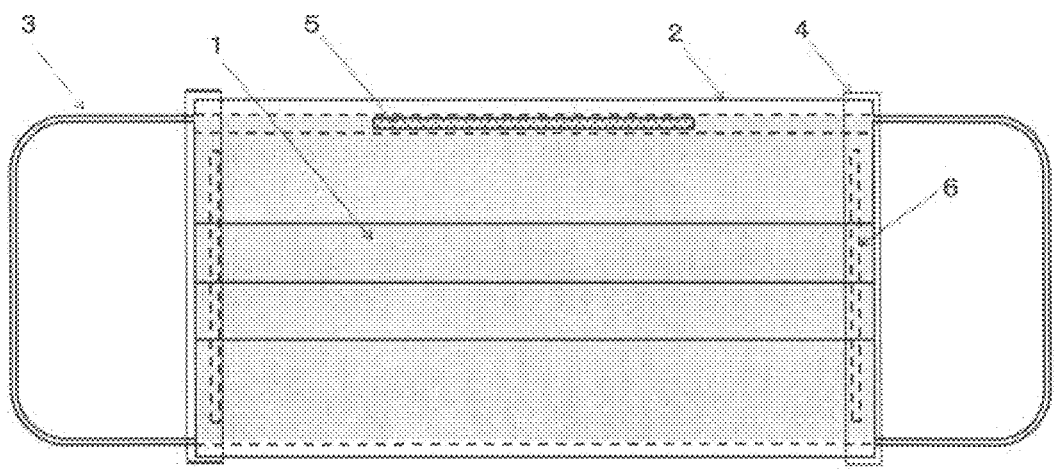
FIG. 1 is a schematic front view of a deodorizing mask of the present invention.

The present invention is a deodorizing mask that includes a mask body provided with a deodorizing nonwoven fabric layer containing a chemisorption-type deodorizer and a dust-proof nonwoven fabric layer having a dust-prevention effect. The dust-proof nonwoven fabric layer has an air permeability equal to or smaller than ⅔ of that of the deodorizing nonwoven fabric layer, and the dust-proof nonwoven fabric layer is provided on the face side of the mask.

A structure of the deodorizing mask of the present invention is not particularly limited so far as the mask is formed in shapes that can cover a wearer's nose and mouth. For example, the mask body may have a flat structure or a three-dimensional structure. Examples of the three-dimensional structure are pleated shape, omega pleated shape, and cup-like shape.

The chemisorption-type deodorizer used in the present invention is a material that deodorizes offensive odors by effecting chemical bonds with a malodorous component included in a malodorous gas to adsorb or decompose the malodorous component. The chemical bonds are not particularly limited, and may rely upon functional groups included in the chemisorption-type deodorizer. Generally, there are different types of deodorizers for use against the malodorous gas, other than deodorizers that adsorb malodorous components through chemisorption such as the chemisorption-type deodorizer according to the present invention. Examples of such deodorizer include a deodorizer which adsorbs a malodorous component through physisorption such as activated carbon, and a deodorizer which decomposes a malodorous gas at a time of contact such as photocatalyst. The deodorizers, when contained and used in the mask body, need to adsorb a malodorous component in short periods of time before the malodorous gas is let through the mask by breathing. Therefore, it fails to obtain satisfactory effects with the physisorption-type deodorizers whose deodorizing rates are low or deodorizers that decompose a malodorous component by irradiating light thereon. Therefore, most suitably used in the deodorizing mask are chemisorption-type deodorizers capable of adsorbing a malodorous component in shorter periods of time at higher deodorizing rates.

In the case of using the chemisorption-type deodorizers, however, it may be difficult for the nonwoven fabric constituting the deodorizing nonwoven fabric layer to be impregnated with large quantities of the deodorizer of this type. Therefore, the chemisorption-type deodorizer according to the present invention preferably has a larger deodorizing capacity and a higher deodorizing rate.

The deodorizing capacity (mL/g) of the chemisorption-type deodorizer represents a quantity of a malodorous component (mL) that can be deodorized by 1 g of the chemisorption-type deodorizer. The deodorizing rate (mL/(0.1 g·min.) of the chemisorption-type deodorizer represents a quantity of a malodorous component (mL) that can be deodorized by 0.1 g of the chemisorption-type deodorizer per minute.

The deodorizing capacity of the chemisorption-type deodorizer per unit mass (g) is preferably equal to or larger than a value obtained by substituting a concentration value (ppm) at the odor intensity grade 5 of the six grades odor intensity measurement method for a unit value of the deodorizing capacity (mL/g).

The odor intensity grades are reference values set forth in the Offensive Odor Control Act, and concentrations corresponding to the odor intensities are defined for different types of malodorous components included in malodorous gases. The odor intensity grades specifically are: 0 for no odor, 1 for barely perceivable odor, 2 for weak but barely discernible odor, 3 for easily discernible odor, 4 for rather strong odor, and 5 for intense odor. For example, concentrations at the odor intensity grade 5 indicating intense odor are: 40 ppm with ammonia, 8 ppm with hydrogen sulfide, 0.2 ppm with methyl mercaptan, 1.9 ppm with acetic acid, and 10 ppm with acetaldehyde.

In this description, the unit used for the gas concentrations, "ppm" is "ppm by volume".

It follows that a preferable lower-limit value of the deodorizing capacity of the chemisorption-type deodorizer is a capacity value obtained by substituting the concentration ppm at the odor intensity grade 5 of a malodorous gas for the unit of mL. With ammonia, 40 ppm is substituted for 40 mL/g. With hydrogen sulfide, 40 ppm is substituted to 8 mL/g. With methyl mercaptan, 40 ppm is substituted for 0.2 mL/g. With acetic acid, 40 ppm is substituted for 1.9 mL/g. With acetaldehyde, 40 ppm is substituted to 10 mL/g. In the case where the content of the chemisorption-type deodorizer in the deodorizing mask is 0.1 g, 4 mL of ammonia can be adsorbed based on the deodorizing capacity of ammonia defined as 40 mL/g. This means that 100 L of a malodorous gas can be deodorized on the whole if the concentration of ammonia is 40 ppm at the odor intensity grade 5, and 400 L of a malodorous gas can be deodorized on the whole if the concentration of ammonia is 10 ppm at the odor intensity grade 4. It further means that 2000 L of a malodorous gas can be deodorized on the whole if the concentration of ammonia is 2 ppm at the odor intensity grade 3. One can accordingly say, as far as the deodorizing mask contains the chemisorption-type deodorizer in a quantity corresponding to or more than the lower-limit value of the deodorizing capacity, its deodorizing effect is well enough for uses in living space. Because the gas concentration at the different odor intensity grade 5 differs depending on types of the malodorous component, preferable lower-limit values of the deodorizing capacity should suitably be decided for any other malodorous components but the mentioned examples and malodorous gases containing them.

A quantity of the malodorous component that can be deodorized by 0.1 g of the chemisorption-type deodorizer per minute is, as described, defined as the deodorizing rate, because it is preferable to use a chemisorption-type deodorizer having a deodorizing rate fast enough to effectively deodorize any odor while respiratory air is passing very fast through the thin mask worn by a wearer in a cross-sectional direction thereof.

The quantity of the malodorous component that can be deodorized by 0.1 g of the chemisorption-type deodorizer per minute, which represents the deodorizing rate of the chemisorption-type deodorizer, is preferably equal to or larger than a quantity included in 10 L of a malodorous gas at the odor intensity grade 5, more preferably equal to or more than twice as much as the quantity, and further preferably equal to or more than quintuple as much as the quantity. An adult's respiratory volume per minute is roughly 10 L. The concentration of ammonia at the odor intensity grade 5 is 40 ppm, and a quantity of ammonia present in the respiratory volume of 10 L (40 ppm×10 L) is 0.4 mL. In the case of using the chemisorption-type deodorizer for adsorption of ammonia, its deodorizing rate is preferably fast enough to make ammonia adsorb to 0.1 g of the deodorizer within a minute. In the event that the deodorizing rate is lower than a quantity of malodorous component included in 10 L of a malodorous gas at the odor intensity grade 5, it is necessary to impregnate the deodorizing nonwoven fabric layer with a large volume of the chemisorption-type deodorizer. This makes it difficult to control a quantity of airflow, possibly affecting comfortableness when the mask is worn and leading to economic disadvantages.

Specific examples of the malodorous component to be deodorized by the chemisorption-type deodorizer include a basic gas such as ammonia and amine; an acid gas such as acetic acid and isovaleric acid; an aldehyde-based gas such as formaldehyde, acetaldehyde, and nonenal; a sulfur-based gas such as hydrogen sulfide and methyl mercaptan; and the like.

The chemisorption-type deodorizer that can be used against these malodorous components may be an inorganic chemisorption-type deodorizer and an organic chemisorption-type deodorizer. Examples of the inorganic chemisorption-type deodorizer include a quadrivalent metal phosphate, an amorphous composite oxide, a synthesized zeolite, and the like. Examples of the organic chemisorption-type deodorizer include a hydrazide compound, and the like. The deodorizers, which are used in masks, are desirably materials which are safe and difficult to degenerate. Preferable examples of the deodorizers are, therefore, inorganic chemisorption-type deodorizers insoluble or poorly soluble in water.

The chemisorption-type deodorizer according to the present invention may be in arbitrary forms, which are not particularly limited. Preferably, a granular chemisorption-type deodorizer is used. A grain size of the deodorizer is not particularly limited, and the deodorizing efficiency increases with finer grain size. Further, the granular deodorizer is advantageously easily treatable to be adhered to nonwoven fabrics, and hardly falls off from the fabrics after the treatment. The median diameter of the chemisorption-type deodorizer according to the present invention measured by a laser diffraction grain size distribution measuring device is preferably in a range from 0.05 to 100 μm, more preferably from 0.1 to 50 μm, and further preferably from 0.2 to 30 μm.

Since the deodorizing effect is improved when contact efficiency of the chemisorption-type deodorizer with a malodorous gas, a specific surface area of the deodorizer is preferably in a range from 10 to 800 $m^2/g$, and more preferably from 30 to 600 $m^2/g$. The specific surface area can be measured from a quantity of adsorbed nitrogen by BET method.

The exemplified chemisorption-type deodorizers may be used singly or in combination of two or more types thereof. Using two different chemisorption-type deodorizers, which are for use against different deodorizing targets (malodorous components), is likely to exert a synergy effect. A suitable combination of the deodorizers against offensive odors generated from, for example, excretion and raw garbage is a chemisorption-type deodorizer for basic gas and a chemisorption-type deodorizer for sulfur-based gas. A suitable combination of the deodorizers against, for example, sweaty odors is a chemisorption-type deodorizer for basic gas and a chemisorption-type deodorizer for acid gas. To deodorize cigarette smoke odors, for example, a chemisorption-type deodorizer for basic gas, a chemisorption-type deodorizer for acid gas, and a chemisorption-type deodorizer for aldehyde-based gas are suitably used in combination. In the case two or more chemisorption-type deodorizers are combined, a ratio of quantities of the chemisorption-type deodorizers is preferably decided based on the deodorizing performances of the chemisorption-type deodorizers to be used such as the deodorizing capacities and deodorizing rates, and a gas concentration of an environment where the deodorizers are used (concentration of malodorous component). To deodorize a malodorous gas containing a plurality of malodorous components using two different chemisorption-type deodorizers, a mass ratio of these deodorizers is 10:90 to 90:10. If the mass ratio of one of the chemisorption-type deodorizers is less than 10% by mass, an adequate deodorizing performance may not be obtained. Some of the chemisorption-type deodorizers, when mixed with each other, may result in a poor deodorizing effect. Therefore, it is necessary to decide whether two chemisorption-type deodorizers should be mixed and subjected to treatments or they should not be mixed but should be separately subjected to treatments. Next, examples of the chemisorption-type deodorizer applicable to the present invention are described below.

(A) Quadrivalent Metal Phosphate

The quadrivalent metal phosphate that can be used as the chemisorption-type deodorizer is preferably a compound represented by the following formula (1). The compound is insoluble or poorly soluble in water and has remarkable deodorizing effects against a basic gas.

$$H_aM_b(PO_4)_c \cdot nH_2O \tag{1}$$

(In the formula, M is a quadrivalent metal, a, b, and c are positive integral numbers satisfying the equation (a+4b=3c), and n is 0 or a positive integral number.)

Preferable examples of the compound include are zirconium phosphate, hafnium phosphate, titanium phosphate, tin phosphate, and the like. These compounds are divided into amorphous compounds and crystalline compounds respectively having different crystal systems such as α-type, β-type, and γ-type crystal systems. Any of these compounds is preferably usable.

(B) Amorphous Composite Oxide

The amorphous composite oxide that can be used as the chemisorption-type deodorizer is preferably an amorphous compound including $Al_2O_3$, $SiO_2$, MgO, CaO, SrO, BaO, ZnO, $ZrO_2$, $TiO_2$, $WO_2$, $CeO_2$, $Li_2O$, $Na_2O$, $K_2O$, or the like. The composite oxide is insoluble or poorly soluble in water and has remarkable deodorizing effects against a basic gas. Particularly preferable examples are amorphous composite oxides represented by $X_2O$—$Al_2O_3$—$SiO_2$ (where X is at least an alkali metal atom selected from Na, K, and Li) by virtue of their remarkable deodorizing performances. Using the amorphous material ensures that evident diffraction signals resulting from a crystalline face are not detected by X-ray powder diffraction. More specifically, signal peaks with high kurtosis (sharp signal peaks) hardly appear in an X-ray diffraction chart where diffraction angles are plotted on the horizontal axis and diffraction signal intensities are plotted on the vertical axis.

(C) Inorganic Compound Carrying Amine Compound

The inorganic compound carrying an amine compound that can be used as the chemisorption-type deodorizer is preferably a hydrazine-based compound which is an organic compound that reacts with an aldehyde-based gas, and an inorganic compound carrying an aminoguanidine salt. The compound has remarkable deodorizing effects against an aldehyde-based gas. Examples of the hydrazine-based compound include dihydrazide adipate, carbohydrazide, dihydrazide succinate, and dihydrazide oxalate. Examples of the aminoguanidine salt include an aminoguanidine hydrochloride, an aminoguanidine sulfate, an aminoguanidine bicarbonate, and the like. Examples of the inorganic compound carrying the amine compound include an amorphous composite oxide, silica gel, a zeolite, and the like.

(D) Hydrated Zirconium Oxide, Zirconium Oxide

The hydrated zirconium oxide and zirconium oxide that can be used as the chemisorption-type deodorizer are preferably amorphous compounds. These compounds are insoluble or poorly soluble in water and have remarkable deodorizing effects against an acid gas. The hydrated zirconium oxide is a compound synonymous with oxy-hydroxylated zirconium, hydroxylated zirconium, water-containing zirconium oxide, and zirconium oxide hydrate.

(E) Active Oxide

The active oxide that can be used as the chemisorption-type deodorizer is preferably an amorphous compound. The active oxide is insoluble or poorly soluble in water and has remarkable deodorizing effects against an acid gas and sulfur-based gas. Specific examples include $Al_2O_3$, $SiO_2$, MgO, CaO, SrO, BaO, ZnO, CuO, MnO, $ZrO_2$, $TiO_2$, $WO_2$, $CeO_2$, and the like. A surface-treated active oxide may be used. Examples of the surface-treated active oxide include an active oxide surface-treated with an organopolysiloxane, and an active oxide surface-coated with aluminum, silicon, zirconium, tin oxide, or hydroxide. For better deodorizing performances, the active oxides are more preferably surface-treated with an organic material such as an organopolysiloxane than an inorganic material.

(F) Hydrotalcite-Based Compound

The hydrotalcite-based compound that can be used as the chemisorption-type deodorizer is preferably a compound having a hydrotalcite structure represented by the following formula (2). The compound is insoluble or poorly soluble in water and has remarkable deodorizing effects against an acid gas.

$$M^1_{(1-x)}M^2_x(OH)_2A^{n-}_{(x/n)} \cdot mH_2O \tag{2}$$

(In the formula, $M^1$ is a bivalent metal ion, $M^2$ is a trivalent metal ion, x is a numeral value larger than 0 and equal to or smaller than 0.5, $A^{n-}$ is an n-valent negative ion such as carbonate ion and sulfate ion, and m is an integral number.)

Examples of the hydrotalcite-based compound include a magnesium-aluminum hydrotalcite, a zinc-aluminum hydrotalcite, and the like. Among these, a magnesium-aluminum hydrotalcite is preferred. The hydrotalcite-based compound includes a hydrotalcite burned product, which is obtained by burning the hydrotalcite-based compound at a temperature equal to or higher than 500° C. until carbonate radicals or hydroxyl groups are desorbed.

(G) Compound Having at Least One Atom Selected from Silver, Copper, Zinc, and Manganese The compound including at least one atom selected from silver, copper, zinc, and manganese that can be used as the chemisorption-type deodorizer is preferably insoluble or poorly soluble in water. The compound has remarkable deodorizing effects against a sulfur-based gas. Examples of the preferable compound including at least one atom selected from silver, copper, zinc, and manganese include an oxide, a hydroxide, a phosphate, and a sulfuric acid; a salt of an organic acid such as acetic acid, oxalic acid, and acrylic acid; a water-insoluble inorganic compound in which at least one atom selected from copper, zinc, and manganese is supported thereon; and the like. Among metals that can be carried by the inorganic compounds, copper, zinc, and manganese are preferably used by virtue of their high deodorizing performances and inexpensiveness. Preferable inorganic compound used as a carrier that supports silver, copper, zinc and manganese includes a quadrivalent metal phosphate, a zeolite, a porous silicon dioxide, and the like.

(H) Zeolite

The zeolite that can be used as the chemisorption-type deodorizer is preferably a synthesized zeolite. The zeolite is insoluble or poorly soluble in water, and has remarkable deodorizing effects against a basic gas. The zeolite may have variously different structures, and any known structures are applicable, which are, for example, A-type, X-type, Y-type, α-type, β-type, ZSM-5, and amorphous structures.

Of the chemisorption-type deodorizers ever mentioned, examples are the following materials whose deodorizing capacities are equal to the mL conversions of the concentrations ppm of malodorous gases at the odor intensity grade 5 and whose deodorizing rates are equal to or larger than quantities included in 10 L of malodorous gases at the odor intensity grade 5; a zirconium phosphate and an amorphous zeolite for ammonia, a $CuO$—$SiO_2$ composite oxide for hydrogen sulfide, a $CuO$—$Al_2O_3$—$SiO_2$ composite oxide for methyl mercaptan, an active zinc oxide for acetic acid and hydrogen sulfide, dihydrazide adipate for acetaldehyde, a water-containing zirconium oxide for isovaleric acid.

The deodorizing nonwoven fabric layer that can be used in the deodorizing mask of the present invention normally has an area dimension ranging from approximately 0.01 to 0.04 $m^2$. When, for example, the deodorizing nonwoven fabric layer having the area dimension of 0.02 $m^2$ is impregnated with 5 $g/m^2$ of the chemisorption-type deodorizer, the content of the chemisorption-type deodorizer is 0.1 g. The content of the chemisorption-type deodorizer in the deodorizing nonwoven fabric layer per unit area is preferably larger. However, larger contents of chemisorption-type deodorizer lead to the problems of an undesirably higher air permeability and cost increase. Therefore, the deodorizer content is preferably decided in view of all these factors. The content of the chemisorption-type deodorizer in the deodorizing nonwoven fabric layer is preferably 1 $g/m^2$ or more, more preferably 3 $g/m^2$ or more, and further preferably 5 $g/m^2$ or more. The content in total of two or more chemisorption-type deodorizers in the deodorizing nonwoven fabric layer is preferably 5 $g/m^2$ or more, more preferably 7 $g/m^2$ or more, and further preferably 9 $g/m^2$ or more. The deodorizing nonwoven fabric layer according to the present invention may be a deodorizing nonwoven fabric layer including multiple layers wherein a plurality of deodorizing nonwoven fabrics constituting the layers are respectively treated with different chemisorption-type deodorizers and then stacked on each other. It is preferable to use a deodorizing nonwoven fabric containing different chemisorption-type deodorizers, where two or more chemisorption-type deodorizers are applied all together or separately applied one after another to one type of nonwoven fabric.

A method for impregnating the deodorizing nonwoven fabric layer with the chemisorption-type deodorizer is not particularly limited, to which any conventional treatment methods are applicable. Examples of the processing method to apply the chemisorption-type deodorizer include incorporating the chemisorption-type deodorizer into fiber, causing a binder such as emulsion and a binder composition containing the chemisorption-type deodorizer to contact the surface of fiber to spread and adhere the chemisorption-type deodorizer onto the surface, and depositing the chemisorption-type deodorizer on the surface of fiber constituting the nonwoven fabric without the use of any binder and securely adhere the deposited chemisorption-type deodorizer thereto by a thermal or chemical treatment. A preferable method among these methods is to spread and adhere the chemisorption-type deodorizer using a binder resin-containing compound, which is an easily-handleable treatment exerting a relatively immediate effect. The binder resin that can be used in the spreading treatment is not particularly limited, and the following resins are available. Specific examples include a natural resin, a natural resin derivative, a phenol resin, a xylene resin, a urea resin, a melamine resin, a ketone resin, a cumarone-indene resin, a petroleum resin, a terpene resin, a cyclized rubber, a chlorinated rubber, an alkyd resin, a polyamide resin, a polyvinyl chloride, an acrylic resin, a vinyl chloride-vinyl acetate copolymer resin, a polyvinyl acetate, a polyvinyl alcohol, a polyvinyl butylal, a chlorinated polypropylene, a styrene resin, an epoxy resin, a urethane-based resin, a cellulose derivative, and the like. Of these examples, an acrylic resin and a urethane-based resin are particularly preferable. The binder resin may be used singly or in combination of two or more types thereof. Preferably used are a binder resin with less odor that can securely adhere the chemisorption-type deodorizer not to fall off from the nonwoven fabric without undermining foldability, heat sealability, and controllability of air permeability of the nonwoven fabric.

In the case of using a binder composition mixedly containing the binder resin and the chemisorption-type deodorizer for the spreading treatment, the content ratio of the chemisorption-type deodorizer relative to an emulsion-derived resin solid content of the binder composition is not particularly limited. The content ratio of the binder resin is preferably larger because the chemisorption-type deodorizer is thereby more securely adhered and even less likely to fall off. On the other hand, the ratio of the resin solid content of the binder resin is preferably smaller to allow the deodorizer to more easily contact a malodorous gas, thereby improving the deodorizing effect. Therefore, the content ratio of the binder resin and the chemisorption-type deodorizer is, respectively, preferably 10% to 90% by mass and 10% to 90% by mass, and more preferably 25% to 60% by mass and 40% to 75% by mass based on 100% by mass of a total mass of the binder resin and the chemisorption-type deodorizer.

When an additive for the binder resin is added to the binder composition containing the chemisorption-type deodorizer, multiple function including the deodorizing performance and improvement for processability to the mask are obtained. Examples of the additive include a dispersant, an anti-foaming agent, a viscosity modifier, a pigment, a dyestuff, an aromatic material, a physisorption-type deodorizer, an antiviral agent, an antifungal agent, an antiallergic agent, and the like. The content of the additive to be combined should be appropriately adjusted depending on intended purposes. More specifically, it is necessary for the additive to be added in such a suitable quantity that does not adversely affect the deodorizing effect of the chemisorption-type deodorizer, physical properties of the deodorizing nonwoven fabric, and processability of the mask.

Any conventional methods for dispersing inorganic powdered materials are applicable to the preparation of the binder composition where the chemisorption-type deodorizer and the binder are combined. For example, an additive, such as a dispersant, is added to an emulsion of an acrylic resin, and a chemisorption-type deodorizer is further added thereto. Then, the resulting material is agitated by means of a sand mill, dispersion mill, or ball mill to disperse them. As the chemisorption-type deodorizer of the binder composition has a larger concentration of solid content, the binder composition increases its viscosity and becomes more difficult to handle, but at the same time, becomes more stable. Therefore, the chemisorption-type deodorizer included in the binder composition preferably has a concentration of solid content in a range from 5% to 60% by mass. To adjust the viscosity of the binder composition, a viscosity modifier may be added thereto to such an extent that does not adversely affect the deodorizing performance.

The binder composition containing the chemisorption-type deodorizer can be spread onto the nonwoven fabric by any suitable conventional method such as dipping, spraying and padding. The dipping is more specifically, for example, still standing at room temperature, and agitating while heating. The padding is more specifically, for example, pad drying, pad steaming, either of which is applicable. The nonwoven fabric thus coated with the prepared material is dried to remove any moisture content therefrom, so that the function of the binder resin supports secure adhesion of the chemisorption-type deodorizer to the nonwoven fabric. A drying temperature at the time, though not particularly limited, should be approximately 50° C. to 150° C., and is preferably approximately 80° C. to 120° C. A length of drying time, which may differ at different temperatures, is preferably in a range from five minutes to 12 hours, and more preferably from ten minutes to two hours. When dried under the specified condition, the chemisorption-type deodorizer can be securely adhered to the nonwoven fabric.

The dust-proof nonwoven fabric layer according to the present invention is not particularly limited as far as the requirement of air permeability is met. Any of dust-proof nonwoven fabrics for dust prevention variously configured can be suitably selected and used depending on intended purposes. The criteria of dust proofness (filterability) with masks differ from one country to another. Generally, nine different standards set by the NIOSH, USA (National Institute of Occupational Safety and Health) are often used. The nine different standards set by the NIOSH are, for example, N95, N99, N100, and R95, which are defined by combinations of three standards of resistance to oils, "N (not resistant to oils)", "R (resistant to oils)", and "P (oil-proof), and degrees of collection efficiency in collecting particulates with sizes of 0.1 to 0.3 µm, "95 (removable by 95% or more)", "99 (removable by 99% or more)", and "100 (removable by 99.7% or more)". There are other indicators for the dust-proof performance of masks, which are for example, BFE (Bacterial Filtration Efficiency) and PFE (Particle Filtration Efficiency). The BFE is a ratio (%) of removal of particles including bacteria by a mask (mean particle size: 4.0 to 5.0 micrometers). The PFE is a ratio (%) of removal of test particles by a mask (latex spherical particles made of polystyrene with particle sizes of 0.1 micrometers). For example, the Food and Drug Administration, USA sets the standard of surgical masks to BFE 95% or more.

Examples of the deodorizing nonwoven fabric and dust-proof nonwoven fabric used to produce the deodorizing mask of the present invention include a spun bond nonwoven fabric, a melt blown nonwoven fabric, a flush spinning nonwoven fabric, a spunlace nonwoven fabric, an airlaid nonwoven fabric, a thermal bond nonwoven fabric, a needle punch nonwoven fabric, a chemical bond nonwoven fabric, a paper, and the like. Examples of a resin constituting fibers included in these nonwoven fabrics include a polyester, a polyethylene, a polypropylene, a polyvinyl chloride, a polyacrylic acid, a polyamide, a polyvinyl alcohol, a polyurethane, a polyvinylester, a polymethacrylic acid ester, a rayon, and the like. When the chemisorption-type deodorizer is spread through the use of the binder, a polyethylene, a polypropylene, a polyester, and a rayon are suitably used in view of adherability of the binder, foldability of the deodorizer-spread nonwoven fabric, and air permeability. The deodorizing nonwoven fabric and the dust-proof nonwoven fabric may be both formed from fibers containing one of these resins or formed from a plurality of resin-made fibers.

A mean diameter of the fibers in the deodorizing nonwoven fabric and the dust-proof nonwoven fabric is normally in a range from 5 to 30 and preferably from 10 to 25 µm.

The deodorizing nonwoven fabric and the dust-proof nonwoven fabric preferably have a mass per unit area of 10 to 90 g/m$^2$. The mass per unit area of 10 g/m$^2$ or below causes the chemisorption-type deodorizer to clog voids of the nonwoven fabric, degrading the air permeability. If the mass per unit area of 90 g/m$^2$ or more, the process of adhering the chemisorption-type deodorizer to the fabric is not as efficient, increasing the mask body in thickness. According to the present invention, the deodorizing nonwoven fabric and the dust-proof nonwoven fabric may both be a multilayered fabric including a plurality of nonwoven fabrics. In that case, values of the mass per unit area of the used nonwoven fabrics in total preferably stay in the foregoing range.

The air permeabilities of the deodorizing and dust-proof nonwoven fabrics can be defined based on values measured by JIS L1096 Frajour type method using Frajour type testing machine. As the mask body according to the present invention increases its air permeability, any resistance against respiratory air reduces, helping a wearer of the mask to breathe more easily. In contrast, the deodorizing effect is more evident with a smaller air permeability of the mask body. A quantity of airflow through the dust-proof nonwoven fabric according to Frajour type method is preferably in a range from 10 to 120 cm$^3$/(cm$^2$·s), and more preferably from 20 to 100 cm$^3$/(cm$^2$·s). A quantity of airflow through the deodorizing nonwoven fabric according to Frajour type method is preferably in a range from 40 to 400 cm$^3$/(cm$^2$·s), and more preferably from 60 to 350 cm$^3$/(cm$^2$·s). A key factor for a better commercial value of the deodorizing mask is a well-balanced relationship between the deodorizing performance and air resistance in the mask body. The present invention is the very first that has ever accomplished such a well-balanced relationship.

The deodorizing mask of the present invention substantially has a deodorizing nonwoven fabric layer containing a chemisorption-type deodorizer and a dust-proof nonwoven fabric layer having a dust-prevention effect, and the dust-proof nonwoven fabric layer has an air permeability equal to or smaller than ⅔ of that of the deodorizing nonwoven fabric layer. The mask thus characterized and having the dust-proof nonwoven fabric layer on its face side achieves an outstanding deodorizing performance against offensive odors and effectively prevents a wearer of the mask from inhaling malodorous gases.

The present invention may provide an additional layer between the deodorizing nonwoven fabric layer and the dust-proof nonwoven fabric layer as far as the effectiveness of the present invention is not thereby adversely affected. The additional layer is not particularly limited as to its shape or material as far as the layer is air-permeable. The additional layer may be a nonwoven fabric layer or a woven fabric layer. Preferably, the additional layer has an air permeability equal to or higher than that of the deodorizing nonwoven fabric layer.

The deodorizing mask of the present invention preferably has a structure where the deodorizing nonwoven fabric layer is adjacent to the dust-proof nonwoven fabric layer. In the case where the deodorizing nonwoven fabric layer is arranged adjacently to the dust-proof nonwoven fabric layer, the effectiveness of the present invention becomes even more efficient. As mentioned earlier, the dust-proof nonwoven fabric layer may have a multilayered structure including a plurality of nonwoven fabrics, and the deodorizing nonwoven fabric layer may have a multilayered structure including a plurality of nonwoven fabrics. The multilayered deodorizing nonwoven fabric layer may include nonwoven fabrics respectively treated with different chemisorption-type deodorizers.

The intended advantage of the present invention is effectuated by a difference between the air permeabilities of the dust-proof nonwoven fabric layer and the deodorizing nonwoven fabric layer. Specifically describing the "difference", the air permeability of the dust-proof nonwoven fabric layer is equal to or smaller than ⅔, preferably equal to or smaller than ½, and more preferably equal to or smaller than ⅖ of that of the deodorizing nonwoven fabric layer in terms of the airflow quantities measured by Frajour type method. A preferable lower limit of the air permeability of the dust-proof nonwoven fabric layer is equal to or smaller than 1/20, and a more preferable lower limit thereof is equal to or smaller than 1/10 of that of the deodorizing nonwoven fabric layer in terms of the airflow quantities measured by Frajour type method. In the case where the dust-proof nonwoven fabric layer and the deodorizing nonwoven fabric layer both have a multilayered structure, the above-described intended advantage of the present invention is effectuated by an overall air permeability of the whole layers.

To produce the deodorizing mask of the present invention, peripheral portions of the deodorizing nonwoven fabric containing the chemisorption-type deodorizer and the dust-proof nonwoven fabric whose air permeability is equal to or smaller than ⅔ of that of the deodorizing nonwoven fabric are bonded to each other except their air-permeable portions (normally, portions surrounded by the peripheral portions). To prevent any displacement of the layered nonwoven fabrics, the mask body peripheral portions, which are not air-impermeable portions, are fixed by, for example, heat seal, bonding, or sewing. Additional nonwoven fabrics may be further provided on the face side and outermost side of the mask body. The additional nonwoven fabrics, though their resin materials are not particularly limited, preferably have air permeabilities equal to or larger than, and more preferably at least twice as much as the air permeabilities of the deodorizing and dust-proof nonwoven fabrics. For example, a water-repellent nonwoven fabric made of polypropylene is preferably used on the outermost side, while a flexible nonwoven fabric made of rayon or polyolefin is preferably used on the face side.

According to the present invention wherein the dust-proof nonwoven fabric layer, whose air permeability is inferior to the other layer, is provided on the face side, intake of air equalizes a negative pressure applied to the deodorizing nonwoven fabric layer. This allows the whole area of the deodorizing nonwoven fabric layer to be equally and effectively used, helping to reduce the concentration of malodorous components in air formed within the mask. In the case where the air permeability of the dust-proof nonwoven fabric layer on the face side is higher than that of the deodorizing nonwoven fabric layer, or the dust-proof nonwoven fabric layer is not provided on the face side, an unfavorable event, which is generally called channeling, probably occurs in parts of the deodorizing nonwoven fabric layer with less pressure loss. This accordingly forms, within the mask, air left with a malodorous component, possibly causing inhalation of the malodorous gas or a shorter life of the deodorizing mask.

The deodorizing mask of the present invention is preferably a three-dimensional mask. The deodorizing mask is required to exert its deodorizing performance on the front side of a user's nasal cavities, and breathability and comfortableness in use are the elements of the mask most highly valued in practical use. To this end, desirable features of the deodorizer are lightness in weight and low resistance against airflow. Therefore, the deodorizer should be used in the nonwoven fabric of the mask in such a limited quantity that can maintain favorable breathability and comfortableness in use. In order to prevent a user from inhaling an odor through gaps between the mask and parts of his/her face uneven in height, the deodorizing mask is preferably three-dimensionally structured so that the user's mouth and nose are completely covered. Preferably, therefore, the mask body is formed in a three-dimensional shape so that the whole mask has a three-dimensional shape that allows the mask to closely fit faces. The three-dimensional shape is, for example, bowl-like shape or cup-like shape, and pleated shape and omega pleated shape formed by folding the non-woven fabrics. Of these shapes, the omega pleated shape is preferable because this shape is easily obtainable with the layered nonwoven fabrics and an effective deodorizing area of the nonwoven fabric can be increased.

Other than the methods for stacking the fabric layers and selecting the nonwoven fabrics constituting the mask body, production of three-dimensional masks thus shaped is a well-known art for those skilled in the art. The shape and dimensions of the pleated mask body can be suitably decided by, for example, modifying a basic rectangular shape of 10 cm×18 cm as illustrated in FIG. 1. Other parts of the mask can employ any suitable ones conventionally available, such as nose wire (wire for shape retention of a peripheral portion of the mask body to fit the shape of a nose), ear hooks, and strengthening seals. Moreover, a conventional heat seal device may be used to put these mask parts together during the production.

The deodorizing mask of the present invention is suitably used in, for example, sewage treatment plants, garbage disposal plants, livestock farms, fertilizer plants, chemical plants, food-processing factories, fishery harbors, health care sites, nursing care sites where handling of excreta is required, sites where cleaning services are provided, zoos where animals are kept, restaurants, and lavatories.

EXAMPLES

Hereinafter, the present invention is further described by ways of Examples. Note that the present invention is not limited to the following Examples.

The median diameter of the chemisorption-type deodorizer was measured based on volumetric basis by a laser diffraction grain size distribution measuring device.

In different tests conducted to evaluate deodorizing performances, gas concentrations were measured by gas detectors respectively designed to detect target gases.

Air permeability was measured by the JIS L1913:2010 Frajour type method and shown in the unit of $cm^3/(cm^2 \cdot s)$. The air permeability of a PP nonwoven fabric (average fiber diameter: 15 µm, mass per unit area: 20 $g/cm^2$) was 220 $cm^3/(cm^2 \cdot s)$. The air permeability of a rayon nonwoven fabric (average fiber diameter: 22 µm, mass per unit area: 25 $g/cm^2$) was 405 $cm^3/(cm^2 \cdot s)$. The air permeability of a PP-PE nonwoven fabric in which PP and PE fibers are combined (average fiber diameter: 20 µm, mass per unit area: 25 $g/cm^2$) was 280 $cm^3/(cm^2 \cdot s)$.

A deodorizing rate test measured deodorizing quantities of a malodorous gas that could be deodorized by 0.1 g of the deodorizer per minute, and the measured deodorizing quantities were evaluated as deodorizing rates.

The deodorizing rate test was conducted as described below.

A tedlar bag, after 0.1 g of a deodorizer was put therein, was tightly sealed. Then, 1 L of malodorous gases concentrated to a concentration 50 times as much as the concentration at the odor intensity grade 5 (ammonia: 2000 ppm, hydrogen sulfide: 400 ppm, methyl mercaptan: 10 ppm, acetic acid: 95 ppm, acetaldehyde: 500 ppm, isovaleric acid: 15 ppm) was added into the tedlar bag. When one minute passed, the concentration of any residual gas was measured by the relevant gas detector. Table 1 shows values of the deodorizing rates [(mL/0.1 g·min.)] and deodorizing capacities (mL/g) of the deodorizers obtained by the following method.

obtained with these five subjects were averaged and used as the odor intensity result of the organoleptic test.
   Odor intensity 0: no odor
   Odor intensity 1: barely perceivable odor
   Odor intensity 2: weak but barely discernible odor
   Odor intensity 3: easily discernible odor
   Odor intensity 4: rather strong odor
   Odor intensity 5: intense odor

TABLE 1

| Deodorizer | Gas (malodorous gas to be deodorized) | Concentration at odor intensity grade 5 [volume ppm] | Deodorizing capacity [mL/g] | Concentration of residual odorous gas [volume ppm] | Deodorizing rate [mL/ (0.1 g · min.)] |
|---|---|---|---|---|---|
| Zirconium phosphate | Ammonia | 40 | 190 | 0 | >2 |
| $CuO$—$SiO_2$ composite oxide | Hydrogen sulfide | 8 | 98 | 0 | >0.4 |
| $CuO$—$Al_2O_3$—$SiO_2$ composite oxide | Methyl mercaptan | 0.2 | 48 | 0 | >0.01 |
| Amorphous zeolite | Ammonia | 40 | 53 | 1100 | 0.9 |
| Active zinc oxide | Hydrogen sulfide | 8 | 108 | 0 | >0.4 |
| Active zinc oxide | Acetic acid | 1.9 | 28 | 0 | >0.095 |
| Dihydrazide adipate | Acetaldehyde | 10 | 38 | 200 | 0.3 |
| Water-containing zirconium oxide | Isovaleric acid | 0.3 | 18 | 0 | >0.015 |
| Activated carbon (physisorption) | Ammonia | 40 | 9.8 | 1700 | 0.3 |

The deodorizing rates were calculated using the equation:

1000 (mL)×(incipient malodorous gas concentration (ppm)−residual gas concentration ppm))×$10^{-6}$/ (0.1 g·min.).

A deodorizing capacity test for calculating a deodorizing capacity was conducted as described below.

A tedlar bag, after 0.01 g of a deodorizer was put therein, was tightly sealed. Then, 2 L of malodorous gases concentrated to a concentration 200 times as much as the concentration at the odor intensity grade 5 (ammonia: 8000 ppm, hydrogen sulfide: 1600 ppm, methyl mercaptan: 40 ppm, acetic acid: 380 ppm, acetaldehyde: 2000 ppm, isovaleric acid: 60 ppm) was added into the tedlar bag. When 24 hours passed, the concentration of any residual gas was measured by the relevant gas detector.

The deodorizing capacity values (mL/g) were calculated using the equation:

2000 (mL)×(incipient malodorous gas concentration (ppm)−residual gas concentration (ppm))×$10^{-6}$/ 0.01 (g).

All of the deodorizers listed in the table 1 were chemisorption-type deodorizers except the activated carbon which was a physisorption-type deodorizer. The deodorizing rate test result demonstrates that these chemisorption-type deodorizers exert deodorizing performances in which 0.1 g of these deodorizers can deodorize 10 L of the malodorous gases per minute at the concentrations of the odor intensity grade 5 of these gases, or even higher deodorizing performances.

A deodorization organoleptic test was conducted, in which odor bags were filled with 1 L of malodorous gases at the concentrations of the odor intensity grade 5 of these gases (ammonia: 40 ppm, hydrogen sulfide: 8 ppm, methyl mercaptan: 0.2 ppm, acetic acid: 1.9 ppm, acetaldehyde: 10 ppm), and five test subjects each wearing the deodorizing mask smelled the inside of these bags to evaluate odor intensities in accordance with the following criteria The odor intensities Reference Example 1

Production of Deodorizing Nonwoven Fabric A

The following materials were respectively used as chemisorption-type deodorizers for ammonia and hydrogen sulfide; zirconium phosphate having a deodorizing capacity of 190 mL/g and a deodorizing rate of 2 mL/(0.1 g·min.) to deodorize an ammonia gas in normal condition, and a $CuO$—$SiO_2$ composite oxide having a deodorizing capacity of 98 mL/g and a deodorizing rate of over 0.4 mL/(0.1 g·min.) to deodorize a hydrogen sulfide gas in normal condition. Then, powders of the zirconium phosphate and $CuO$—$SiO_2$ composite oxide, and an acrylic emulsion were used to prepare a deodorizer-containing acrylic emulsion A having a solid content concentration of 10% by mass. The mass ratios of these materials contained in the emulsion were; 2 parts of the zirconium phosphate, 6 parts of the $CuO$—$SiO_2$ composite oxide, and 5 parts of the resin solid content of the acrylic emulsion. The deodorizer-containing acrylic emulsion A was applied evenly to a nonwoven fabric containing rayon fiber by 60% by mass, PP fiber by 20% by mass, and PET fiber by 20% by mass (mean fiber diameter: 18 μm, mass per unit area: 50 g/cm$^2$). The emulsion A was applied so as to spread 2 g/m$^2$ of the zirconium phosphate and 6 g/m$^2$ of the $CuO$—$SiO_2$ composite oxide. Then, the fabric was dried to obtain a deodorizing nonwoven fabric A. A quantity of airflow through the deodorizing nonwoven fabric A measured by Frajour type method was 188 cm$^3$/(cm$^2$·s) (see Table 2).

Reference Example 2

Production of Deodorizing Nonwoven Fabric B

The following materials were respectively used as chemisorption-type deodorizers for ammonia and methyl mercaptan; zirconium phosphate having a deodorizing capacity of 190 mL/g and a deodorizing rate of 2 mL/(0.1 g·min.) to deodorize an ammonia gas in normal condition, and a CuO—$Al_2O_3$—$SiO_2$ composite oxide having a deodorizing capacity of 48 mL/g and a deodorizing rate of over 0.01 mL/(0.1 g·min.) to deodorize a methyl mercaptan gas in normal condition. Then, powders of the zirconium phosphate and CuO—$Al_2O_3$—$SiO_2$ composite oxide, and an acrylic emulsion were used to prepare a deodorizer-containing acrylic emulsion B having a solid content concentration of 10% by mass. The mass ratios of these materials contained in the emulsion were; 4 parts of the zirconium phosphate, 4 parts of the CuO—$Al_2O_3$—$SiO_2$ composite oxide, 3 parts of the resin solid content of the acrylic emulsion. The deodorizer-containing acrylic emulsion B was applied evenly to a nonwoven fabric containing rayon fiber by 60% by mass, PE fiber by 30% by mass, and PET fiber by 10% by mass (mean fiber diameter: 16 μm, mass per unit area: 45 g/cm$^2$). The emulsion B was applied so as to spread 4 g/m$^2$ of the zirconium phosphate and 4 g/m$^2$ of the CuO—$Al_2O_3$—$SiO_2$ composite oxide. Then, the fabric was dried to obtain a deodorizing nonwoven fabric B. A quantity of airflow through the deodorizing nonwoven fabric B measured by Frajour type method was 246 cm$^3$/(cm$^2$·s) (see Table 2).

Reference Example 3

Production of Deodorizing Nonwoven Fabric C

The following materials were respectively used as chemisorption-type deodorizers for ammonia, acetic acid, and aldehyde; amorphous zeolite having a deodorizing capacity of 53 mL/g and a deodorizing rate of 0.9 mL/(0.1 g·min.) to deodorize an ammonia gas in normal condition, an active zinc oxide having a deodorizing capacity of 28 mL/g and a deodorizing rate of over 0.095 mL/(0.1 g·min.) to deodorize an acetic acid gas in normal condition, and a silica gel carrying dihydrazide adipate by 30% having a deodorizing capacity of 38 mL/g and a deodorizing rate of 0.3 mL/(0.1 g·min.) to deodorize an acetaldehyde gas in normal condition. Then, powders of the amorphous zeolite, active zinc oxide, and silica gel carrying dihydrazide adipate by 30%, and an acrylic emulsion were used to prepare a deodorizer-containing acrylic emulsion C having a solid content concentration of 10% by mass. The mass ratios of these materials contained in the emulsion were; 2 parts of the amorphous zeolite, 4 parts of the active zinc oxide, 2 parts of the silica gel carrying dihydrazide adipate by 30%, and 6 parts of the resin solid content of the acylyric emulsion. The deodorizer-containing acrylic emulsion C was applied evenly to a nonwoven fabric containing rayon fiber by 60% by mass, PP fiber by 20% by mass, and PET fiber by 20% by mass (mean fiber diameter: 17 μm, mass per unit area: 48 g/cm$^2$). The emulsion C was applied so as to spread 2 g/m$^2$ of the zirconium phosphate, 4 g/m$^2$ of the active zinc oxide, and 2 g/m$^2$ of the silica gel carrying dihydrazide adipate by 30%. Then, the fabric was dried to obtain a deodorizing nonwoven fabric C. A quantity of airflow through the deodorizing nonwoven fabric C measured by Frajour type method was 190 cm$^3$/(cm$^2$·s) (see Table 2).

Reference Example 4

Production of Deodorizing Nonwoven Fabric D

The following materials were respectively used as chemisorption-type deodorizers for ammonia and isovaleric acid; zirconium phosphate having a deodorizing capacity of 190 mL/g and a deodorizing rate of 2 mL/(0.1 g·min.) to deodorize an ammonia gas in normal condition, and oxy-hydroxylated zirconium (also known as water-containing zirconium oxide) having a deodorizing capacity of 18 mL/g and a deodorizing rate of over 0.015 mL/(0.1 g·min.) to deodorize an isovaleric acid gas in normal condition. Then, powders of the zirconium phosphate and oxy-hydroxylated zirconium, and an acrylic emulsion were used to prepare a deodorizer-containing acrylic emulsion D having a solid content concentration of 10% by mass. The mass ratios of these materials contained in the emulsion were; 3 parts of the zirconium phosphate, 3 parts of the oxy-hydroxylated zirconium, and 4 parts of the resin solid content of the acrylic emulsion. The deodorizer-containing acrylic emulsion D was applied evenly to a nonwoven fabric containing rayon fiber by 60% by mass, PP fiber by 20% by mass, and PET fiber by 20% by mass (mean fiber diameter: 15 μm, mass per unit area: 40 g/cm$^2$). The emulsion D was applied so as to spread 3 g/m$^2$ of the zirconium phosphate and 3 g/m$^2$ of the oxy-hydroxylated zirconium. Then, the fabric was dried to obtain a deodorizing nonwoven fabric D. A quantity of airflow through the deodorizing nonwoven fabric D measured by Frajour type method was 211 cm$^3$/(cm$^2$·s) (see Table 2).

Reference Example 5

Production of Deodorizing Nonwoven Fabric E

As a physisorption-type deodorizer for ammonia, an activated carbon was used, having a deodorizing capacity of 9.8 mL/g and a deodorizing rate of 0.3 mL/(0.1 g·min.) to deodorize an ammonia gas in normal condition. Then, the activated carbon and an acrylic emulsion were used to prepare a deodorizer-containing acrylic emulsion E having a solid content concentration of 10% by mass. The mass ratios of these materials contained in the emulsion were; 5 parts of the activated carbon, and 4 parts of the resin solid content of the acrylic emulsion. The deodorizer-containing acrylic emulsion E was applied evenly to a nonwoven fabric containing rayon fiber by 60% by mass, PP fiber by 20% by mass, and PET fiber by 20% by mass (mean fiber diameter: 18 μm, mass per unit area: 50 g/cm$^2$). The emulsion E was applied so as to spread 5 g/m$^2$ of the activated carbon. Then, the fabric was dried to obtain a deodorizing nonwoven fabric E. A quantity of airflow through the deodorizing nonwoven fabric E measured by Frajour type method was 251 cm$^3$/(cm$^2$·s) (see Table 2).

Reference Example 6

Production of Deodorizing Nonwoven Fabric J

The deodorizer-containing acrylic emulsion A prepared as Reference Example 1 was applied evenly to a nonwoven fabric containing PE fiber by 60% by mass, PP fiber by 20% by mass, and PET fiber by 20% by mass (mean fiber diameter: 18 μM, mass per unit area: 50 g/cm$^2$). The emulsion A was applied so as to spread 2 g/m$^2$ of the zirconium phosphate and 6 g/m$^2$ of the CuO—$SiO_2$ composite oxide. Then, the fabric was dried to obtain a deodorizing nonwoven fabric J. A quantity of airflow through the deodorizing nonwoven fabric J measured by Frajour type method was 210 cm$^3$/(cm$^2$·s) (see Table 2).

TABLE 2

| | Deodorizing nonwoven fabric | Deodorizer | Content of deodorizer [g/m²] | Frajour type method quantity of airflow [cm³/(cm²·s)] |
|---|---|---|---|---|
| Reference Example 1 | A | Zirconium phosphate<br>CuO—SiO₂ composite oxide | 2<br>6 | 188 |
| Reference Example 2 | B | Zirconium phosphate<br>CuO—Al₂O₃—SiO₂ composite oxide | 4<br>4 | 246 |
| Reference Example 3 | C | Amorphous zeolite<br>Active zinc oxide<br>Dihydrazide adipate | 2<br>4<br>2 | 190 |
| Reference Example 4 | D | Zirconium phosphate<br>Water-containing zirconium oxide | 3<br>3 | 211 |
| Reference Example 5 | E | Activated carbon | 5 | 251 |
| Reference Example 6 | J | Zirconium phosphate<br>CuO—SiO₂ composite oxide | 2<br>6 | 210 |

Reference Example 7

Dust-Proof Nonwoven Fabric

A nonwoven fabric formed of rayon fiber by 70% by mass, PP fiber by 10% by mass, and PET fiber by 20% by mass was used as a dust-proof nonwoven fabric.
(1) Dust-Proof Nonwoven Fabric F
Mass per unit area: 25 g/cm², Frajour type quantity of airflow: 56 cm³/(cm²·s)
(2) Dust-Proof Nonwoven Fabric G
Mass per unit area: 20 g/cm², Frajour type quantity of airflow: 146 cm³/(cm²·s)
(3) Dust-Proof Nonwoven Fabric H
Mass per unit area: 25 g/cm², Frajour type quantity of airflow: 98 cm³/(cm²·s)
(4) Dust-Proof Nonwoven Fabric I
Mass per unit area: 20 g/cm², Frajour type quantity of airflow: 411 cm³/(cm²·s)

Example 1

Figure 2:
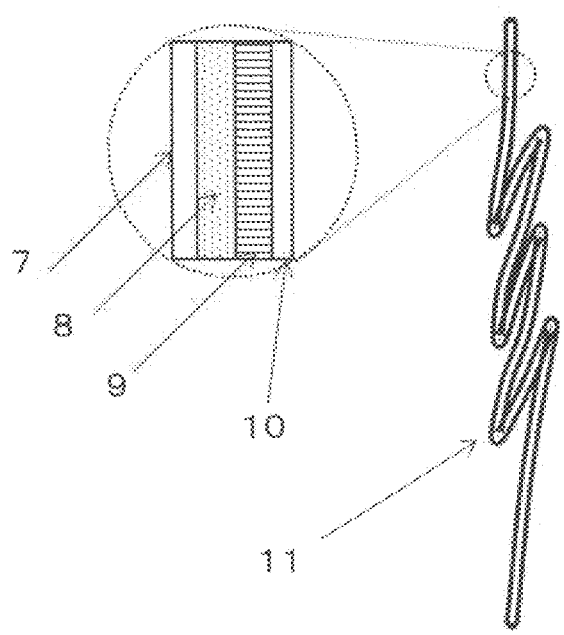
FIG. 2 provides a schematic sectional view of the deodorizing mask of the present invention and an enlarged sectional view of a deodorizing mask according to Example 1.

A PP nonwoven fabric, deodorizing nonwoven fabric A obtained in Reference Example 1, dust-proof nonwoven fabric F obtained in Reference Example 6, and a rayon nonwoven fabric, each having dimensions of 16 cm×18 cm, were stacked in this order to form a four-layer structure. Then, these four layered fabrics were subjected to a pleating work to be folded with three pleats so that the layered fabrics had a rectangular shape in the dimensions of 10 cm×18 cm. With a nose wire being inserted in an edge of the layered structure (center part on numeral-2 side in FIG. 1), its peripheral portion is subjected to a heat seal treatment by using a supersonic sealing apparatus to produce a mask body 1. After ear hooks 3 were fixed at both end parts of the mask body 1 by heat seal, the end parts were end-sealed with heat seal sheets for strengthening and subjected to the heat seal treatment. As a result, a three-dimensional deodorizing mask with three pleats was obtained (see FIGS. 1 and 2). Other than the methods for stacking layers and selecting the nonwoven fabrics constituting the mask body 1, production of such a three-dimensional mask is a well-known art for those skilled in the art. The conventional materials and the apparatus were used to form the ear hooks 3. An organoleptic test was conducted, in which the obtained deodorizing mask was used to deodorize ammonia and hydrogen sulfide. Table 3 shows the result of measured odor intensities as to the odorous gases.

Example 2

Similarly to Example 1, a PP nonwoven fabric, deodorizing nonwoven fabric B obtained in Reference Example 2, dust-proof nonwoven fabric G, and a rayon nonwoven fabric were stacked in this order to form a four-layer structure. Then, these four layered fabrics were formed into a three-dimensional mask with three pleats. An organoleptic test was conducted, in which the obtained deodorizing mask was used to deodorize ammonia and methyl mercaptan. Table 3 shows the result of measured odor intensities as to the odorous gases.

Example 3

Similarly to Example 1, a PP nonwoven fabric, deodorizing nonwoven fabric C obtained in Reference Example 3, dust-proof nonwoven fabric F, and a rayon nonwoven fabric were stacked to form a four-layer structure. Then, these four layered fabrics were formed into a three-dimensional mask with three pleats. An organoleptic test was conducted, in which the obtained deodorizing mask was used to deodorize ammonia, acetic acid, and acetaldehyde. Table 3 shows the result of measured odor intensities as to the odorous gases.

Example 4

Similarly to Example 1, a PP nonwoven fabric, deodorizing nonwoven fabric D obtained in Reference Example 4, dust-proof nonwoven fabric H, and a rayon nonwoven fabric were stacked to form a four-layer structure. Then, these four layered fabrics were formed into a three-dimensional mask with three pleats. An organoleptic test was conducted, in which the obtained deodorizing mask was used to deodorize ammonia and isovaleric acid. Table 3 shows the result of measured odor intensities as to the odorous gases.

Example 5

Similarly to Example 1, the deodorizing nonwoven fabric J obtained in Reference Example 6, a PP-PE-combined nonwoven fabric, dust-proof nonwoven fabric F, and a PP-PE-combined nonwoven fabric were stacked to form a four-layer structure. Then, these four layered fabrics were formed into a three-dimensional mask with three pleats. An organoleptic test was conducted, in which the obtained deodorizing mask was used to deodorize ammonia and isovaleric acid. Table 3 shows the result of measured odor intensities as to the odorous gases.

Example 6

Figure 3:
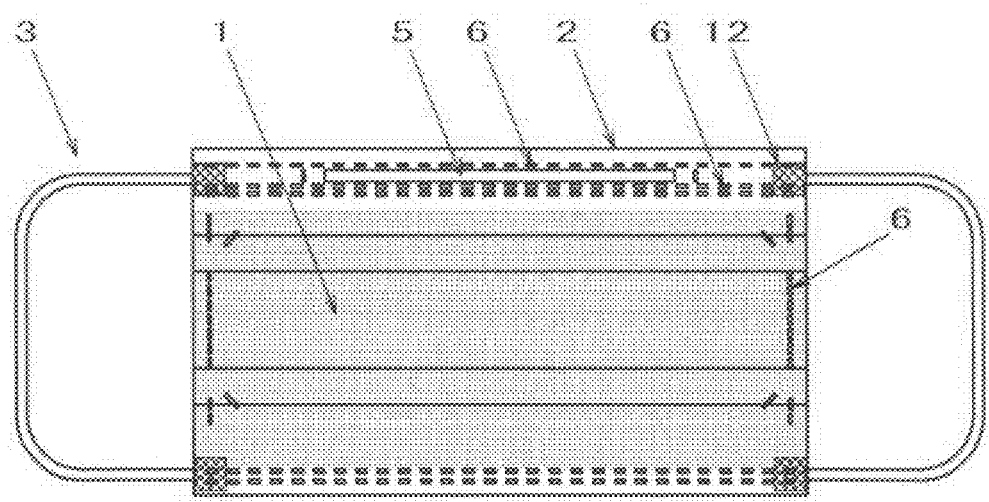
FIG. 3 is a schematic front view of another deodorizing mask of the present invention.
Figure 4:
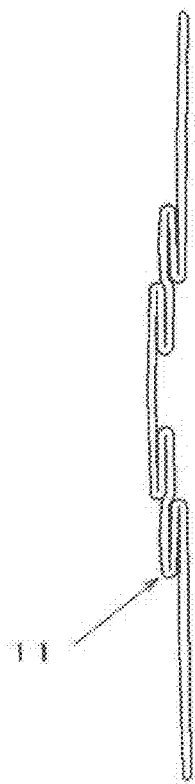
FIG. 4 is a schematic cross-sectional view of the another deodorizing mask of the present invention.

Similarly to Example 1, a PP nonwoven fabric, deodorizing nonwoven fabric J obtained in Reference Example 6, dust-proof nonwoven fabric F obtained in Reference Example 7, and a PP-PE-combined nonwoven fabric, each having the dimensions of 16 cm×18 cm, were stacked in this order to form a four-layer structure. Then, these four layered fabrics were subjected to a pleating work to be folded with three omega pleats so that the layered fabrics had a rectangular shape in the dimensions of 10 cm×18 cm. With a nose wire being inserted in an edge of the layered structure (center part on numeral-2 side in FIG. 1), its peripheral portion is subjected to a heat seal treatment by using a supersonic sealing apparatus to produce a mask body 1. After ear hooks 3 were fixed at both end parts of the mask body 1 with a heat seal mesh, and a heat seal seam 6 was formed at a peripheral edge. As a result, a three-dimensional deodorizing mask with three omega pleats was obtained (see FIGS. 3 and 4). Other than the methods for stacking layers and selecting the nonwoven fabrics constituting the mask body 1, production of such a three-dimensional mask is a well-known art for those skilled in the art. The conventional materials and the apparatus were used to form the ear hooks 3. The obtained deodorizing mask was examined in the deodorization organoleptic test for ammonia and hydrogen sulfide. Table 3 shows the result of measured odor intensities as to the odorous gases.

Example 7

Figure 5:
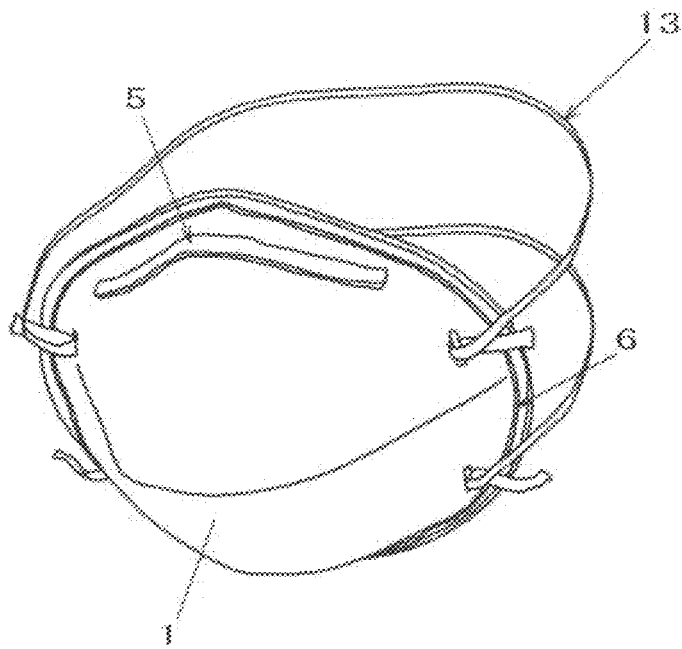
FIG. 5 is a schematic front perspective view of yet another deodorizing mask of the present invention.
Figure 6:
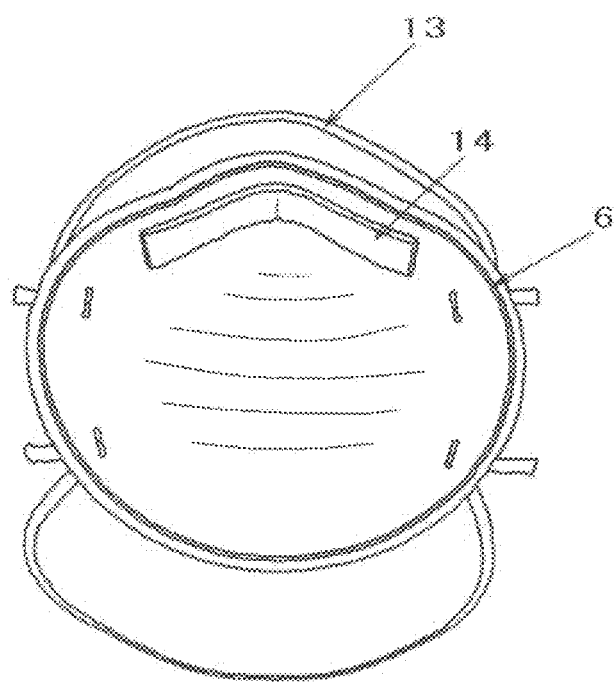
FIG. 6 is a schematic rear view of the yet another deodorizing mask of the present invention.

A PP nonwoven fabric, deodorizing nonwoven fabric J obtained in Reference Example 6, dust-proof nonwoven fabric F obtained in Reference Example 7, and a PP-PE-combined nonwoven fabric were stacked in this order to form a four-layer structure. Then, the layered fabrics were subjected to a work to have the dimensions of 12 cm in height and 14 cm in width. As a result, a cup-shaped deodorizing mask was produced (see FIGS. 5 and 6). An organoleptic test was conducted, in which the obtained deodorizing mask was used to deodorize ammonia and hydrogen sulfide. Table 3 shows the result of measured odor intensities as to the odorous gases.

Comparative Example 1

A three-dimensional mask with three pleats was produced by stacking three fabrics; a PP nonwoven fabric, dust-proof nonwoven fabric F, and a rayon nonwoven fabric from the outermost side of the mask. An organoleptic test was conducted, in which the obtained deodorizing mask was used to deodorize ammonia and hydrogen sulfide. Table 4 shows the result of measured odor intensities as to the odorous gases.

Comparative Example 2

A three-dimensional mask with three pleats was obtained from the deodorizing nonwoven fabric A of Reference Example 1 alone. An organoleptic test was conducted, in which the obtained deodorizing mask was used to deodorize ammonia and hydrogen sulfide. Table 4 shows the result of measured odor intensities as to the odorous gases.

Comparative Example 3

A three-dimensional mask with three pleats was produced by stacking four fabrics; a PP nonwoven fabric, deodorizing nonwoven fabric E obtained in Reference Example 5, dust-proof nonwoven fabric F, and a rayon nonwoven fabric from the outermost side of the mask. An organoleptic test was conducted, in which the obtained deodorizing mask was used to deodorize ammonia and hydrogen sulfide. Table 4 shows the result of measured odor intensities as to the odorous gases.

Comparative Example 4

A three-dimensional mask with three pleats was produced by stacking four fabrics; a PP nonwoven fabric, dust-proof nonwoven fabric F, deodorizing nonwoven fabric A obtained in Reference Example 1, and a rayon nonwoven fabric from the outermost side of the mask. An organoleptic test was conducted, in which the obtained deodorizing mask was used to deodorize ammonia and hydrogen sulfide. Table 4 shows the result of measured odor intensities as to the odorous gases.

Comparative Example 5

A three-dimensional mask with three pleats was produced by stacking three fabrics; deodorizing nonwoven fabric A obtained in Reference Example 1, dust-proof nonwoven fabric I, and a rayon nonwoven fabric in this order from the outermost side of the mask. An organoleptic test was conducted, in which the obtained deodorizing mask was used to deodorize ammonia and hydrogen sulfide. Table 4 shows the result of measured odor intensities as to the odorous gases.

Comparative Example 6

A three-dimensional mask with three pleats was produced by stacking three fabrics; a PP nonwoven fabric, deodorizing nonwoven fabric A obtained in Reference Example 1, and a rayon nonwoven fabric from the outermost side of the mask. An organoleptic test was conducted, in which the obtained deodorizing mask was used to deodorize ammonia and hydrogen sulfide. Table 4 shows the result of measured odor intensities as to the odorous gases.

Mask Structures and Organoleptic Test Results

TABLE 3

| | Nonwoven fabric structure of deodorizing mask body (outermost side/face side) | Deodorizing nonwoven fabric and air permeability [$cm^3/(cm^2 \cdot s)$] | Dust-proof nonwoven fabric and air permeability [$cm^3/(cm^2 \cdot s)$] | Organolepti test Tested malodorous gas | Odor intensity result |
|---|---|---|---|---|---|
| Example 1 | PP layer/Deodorizing layer/ | A | F | Ammonia | 0 |
| | Dust-proof layer/Rayon layer | 188 | 56 | Hydrogen sulfide | 0.2 |
| Example 2 | Deodorizing layer/ | B | G | Ammonia | 0 |
| | Dust-proof layer/Rayon layer | 246 | 146 | Methyl mercaptan | 0.6 |

TABLE 3-continued

|  | Nonwoven fabric structure of deodorizing mask body (outermost side/face side) | Deodorizing nonwoven fabric and air permeability [cm³/(cm²·s)] | Dust-proof nonwoven fabric and air permeability [cm³/(cm²·s)] | Organolepti test Tested malodorous gas | Odor intensity result |
|---|---|---|---|---|---|
| Example 3 | PET layer/Deodorizing layer/ Dust-proof layer/Rayon layer | C 190 | F 56 | Ammonia Acetic acid Acetaldehyde | 0 0.8 0.4 |
| Example 4 | PP layer/Deodorizing layer/ Dust-proof layer/Rayon layer | D 211 | H 98 | Ammonia Isovaleric acid | 0 0.4 |
| Example 5 | Deodorizing layer/ PP-PE layer/Dust-proof layer/ PP-PE layer | J 210 | F 56 | Ammonia Hydrogen sulfide | 0 0.4 |
| Example 6 (omega) | PP layer/Deodorizing layer/ Dust-proof layer/PP-PE layer | J 210 | F 56 | Ammonia Hydrogen sulfide | 0 0.2 |
| Example 7 (cup-shaped) | PP layer/Deodorizing layer/ Dust-proof layer/PP-PE layer | J 210 | F 56 | Ammonia Hydrogen sulfide | 0 0.2 |

TABLE 4

|  | Nonwoven fabric structure of deodorizing mask body (outermost side/face side) | Deodorizing nonwoven fabric and air permeability [cm³/(cm²·s)] | Dust-proof nonwoven fabric and air permeability [cm³/(cm²·s)] | Organoleptic test Tested malodorous gas | Odor intensity result |
|---|---|---|---|---|---|
| Comparative Example 1 | PP layer/Dust-proof layer/ Rayon layer | — | F 56 | Ammonia Hydrogen sulfide | 5.0 5.0 |
| Comparative Example 2 | Deodorizing layer alone | A 188 | — | Ammonia Hydrogen sulfide | 2.2 2.6 |
| Comparative Example 3 | PP layer/Deodorizing layer/ Dust-proof layer/Rayon layer | E 251 | F 56 | Ammonia | 4.6 |
| Comparative Example 4 | PP layer/Dust-proof layer/ Deodorizing layer/Rayon layer | A 188 | F 56 | Ammonia Hydrogen sulfide | 1.2 2.8 |
| Comparative Example 5 | Deodorizing layer/ Dust-proof layer | A 188 | I 411 | Ammonia Hydrogen sulfide | 2.0 2.0 |
| Comparative Example 6 | PP layer/Deodorizing layer/ Rayon layer | A 188 | — | Ammonia Hydrogen sulfide | 2.2 2.2 |

Referring to Tables 3 and 4, any columns with (−) relating to the deodorizing and dust-proof nonwoven fabrics indicate that these fabrics were not used in the relevant layered structures. All of the odor intensity average results obtained from the organoleptic tests of Examples 1 to 6 showed values smaller than 1. This is a range of values where the malodors are scarcely perceived. In Comparative Example 2 and Example 1, although the same deodorizing nonwoven fabric A was used, no malodor was perceived in Example 1, whereas the odor intensity in the range of 2.2 to 2.6 was obtained in Comparative Example 2. These results demonstrate the significance of providing the dust-proof nonwoven fabric layer on the face side of the mask body in addition to the deodorizing nonwoven fabric; otherwise, the deodorizing performance would become less effective.

In Comparative Example 5, the deodorizing nonwoven fabric layer is provided on the face side of the mask relative to the dust-proof nonwoven fabric layer. The deodorizing performance of Comparative Example 5 is proven to be less effective than the examples of the present invention.

Comparative Example 6 provided the fabric structure of the mask body where the dust-proof nonwoven fabric layer had an air permeability higher than that of the deodorizing nonwoven fabric layer, which does not meet the air-permeability requirement of 2/3 or below. The deodorizing performance of this comparative example was proven to be inferior to Example 1. These facts strongly suggest that the ratio of the air permeabilities of the deodorizing nonwoven fabric layer and the dust-proof nonwoven fabric layer is a deciding factor on whether the intended advantage of this invention is achievable.

Example 5 provided the PP-PE-combined nonwoven fabric between the deodorizing nonwoven fabric layer and the dust-proof nonwoven fabric layer. As to Example 5, though the result with hydrogen sulfide is ranked slightly lower than Example 1, its overall deodorizing effect is satisfactory.

The mask of Example 6 had a three-dimensional structure with three omega pleats. The mask of Example 6 was a better fitting mask with an outstanding deodorizing effect similar to Example 1.

Example 7 provided the three-dimensional mask formed in a cup-like shape. As with Example 1, the mask of Example 7 was a better fitting mask with an outstanding deodorizing effect.

Comparative Example 3 is similar to some of the examples as to the order of stacking the deodorizing nonwoven fabric layer and the dust-proof nonwoven fabric layer. Comparative Example 3 using the activated carbon, which is not a chemisorption-type deodorizer, however, resulted in a considerably poor deodorizing effect. In Comparative Example 4, the dust-proof nonwoven fabric layer is provided on the outer side of the mask than the deodorizing nonwoven fabric layer. The deodorizing performance of Comparative Example 4 was inferior to Example 1, which demonstrates that the deodorizing effect is largely affected by the order of stacking the deodorizing nonwoven fabric layer and the dust-proof nonwoven fabric layer.

INDUSTRIAL APPLICABILITY

The present invention provides a deodorizing mask or an odor-preventive mask capable of exerting a deodorizing effect in environments with malodorous gases to such an extent that offensive odors generated by, for example, excreta or putrescence are no longer perceived immediately after the mask is put on. The deodorizing mask is advantageously used in operations at sites where offensive odors are generated, such as excreta disposal plants, sewage-associated treatment plants, livestock farms, garbage disposal plants, fertilizer plants, chemical plants, fishery harbors, health care sites, nursing care sites, disaster-stricken sites for removal of remains, and corpse treatment facilities.

DESCRIPTION OF THE REFERENCE NUMERAL

1. Mask body
2. Upper part of mask body
3. Ear hook
4. End seal
5. Nose wire
6. Heat seal seam
7. PP nonwoven fabric on outermost side
8. Deodorizing nonwoven fabric layer
9. Dust-proof nonwoven fabric layer
10. Rayon nonwoven fabric on face side
11. Pleat
12. Heat seal mesh
13. Neck-hang string
14. Nose pad

What is claimed is:

1. A deodorizing mask having an air permeability and comprising a mask body for covering a wearer's nose and mouth with at least two types of nonwoven fabrics,
    wherein said mask body comprises a deodorizing nonwoven fabric layer including a chemisorption-type deodorizer and a dust-proof nonwoven fabric layer having a dust-prevention effect,
    wherein said dust-proof nonwoven fabric layer has an air permeability equal to or smaller than ⅔ of an air permeability of said deodorizing nonwoven fabric layer, and
    wherein said dust-proof nonwoven fabric layer is provided on a face side of said deodorizing mask relative to said deodorizing nonwoven fabric layer, and
    wherein said chemisorption-type deodorizer is at least one component selected from the group consisting of zirconium phosphate, $CuO$—$SiO_2$ composite oxide, $CuO$—$Al_2O_3$—$SiO_2$ amorphous zeolite, active zinc oxide, dihydrazide adipate and hydrated zirconium oxide.

2. The deodorizing mask according to claim 1,
    wherein said air permeability of said dust-proof nonwoven fabric layer measured by Frajour type method is in a range from 10 to 120 $cm^3/(cm^2 \cdot s)$,
    wherein said air permeability of said deodorizing nonwoven fabric layer measured by Frajour type method is in a range from 40 to 400 $cm^3/(cm^2 \cdot s)$, and
    wherein said air permeability of said dust-proof nonwoven fabric layer is equal to or smaller than ⅔ of said air permeability of said deodorizing nonwoven fabric layer.

3. The deodorizing mask according to claim 1,
    wherein said chemisorption-type deodorizer is a deodorizer in which a quantity of malodorous component that can be deodorized by 0.1 g of said chemisorption-type deodorizer per minute is equal to or larger than a quantity of malodorous component included in 10 L of a malodorous gas at odor intensity grade 5 of a six grades odor intensity measurement method, and
    wherein a content of said chemisorption-type deodorizer contained in said deodorizing nonwoven fabric layer is 1 $g/m^2$ or more.

4. The deodorizing mask according to claim 1,
    wherein said deodorizing nonwoven fabric layer includes at least two different chemisorption-type deodorizers.

5. The deodorizing mask according to claim 1,
    wherein said chemisorption-type deodorizer contained in said deodorizing nonwoven fabric layer is adhered with a binder resin, and
    wherein content ratios of said binder resin and said chemisorption-type deodorizer are respectively 10% to 90% by mass and 10% to 90% by mass based on 100% by mass of a total content of said binder resin and said chemisorption-type deodorizer.

6. The deodorizing mask according to claim 1,
    wherein said deodorizing nonwoven fabric is composed of at least one selected from an olefin resin, a polyester resin, and rayon.

7. The deodorizing mask according to claim 1, having a structure in which said deodorizing nonwoven fabric layer and said dust-proof nonwoven fabric layer are adjacent to each other.

8. The deodorizing mask according to claim 1,
    wherein said chemisorption-type deodorizer comprises dihydrazide adipate.

9. The deodorizing mask according to claim 1,
    wherein said chemisorption-type deodorizer comprises a hydrated zirconium oxide.

10. The deodorizing mask according to claim 1,
    wherein said chemisorption-type deodorizer is zirconium phosphate.

11. The deodorizing mask according to claim 1,
    wherein said chemisorption-type deodorizer comprises at least two components selected from a group consisting of zirconium phosphate, $CuO$—$SiO_2$ composite oxide, $CuO$—$Al_2O_3$—$SiO_2$ composite oxide, amorphous zeolite, active zinc oxide, dihydrazide adipate, and hydrated zirconium oxide.

12. The deodorizing mask according to claim 11,
    wherein said chemisorption-type deodorizer consists of zirconium phosphate and $CuO$—$SiO_2$ composite oxide.

13. The deodorizing mask according to claim 11,
    wherein said chemisorption-type deodorizer consists of zirconium phosphate and $CuO$—$Al_2O_3$-$SiO_2$ composite oxide.

14. The deodorizing mask according to claim 11,
    wherein said chemisorption-type deodorizer consists of amorphous zeolite, active zinc oxide and dihydrazide adipate.

15. The deodorizing mask according to claim 11,
    wherein said chemisorption-type deodorizer consists of zirconium phosphate and hydrated zirconium oxide.

16. The deodorizing mask according to claim 1, wherein said chemisorption-type deodorizer comprises $CuO$—$SiO_2$ composite oxide.

17. The deodorizing mask according to claim 1, wherein said chemisorption-type deodorizer comprises $CuO$—$Al_2O_3$—$SiO_2$ amorphous zeolite.

18. The deodorizing mask according to claim 1, wherein said chemisorption-type deodorizer comprises active zinc oxide.

19. The deodorizing mask according to claim 1, wherein said air permability of said dust-proof nonwoven fabric layer measured by Frajour type method is in the range from 20 to 46 $cm^3/(cm^2 \cdot s)$, said air permability of said deodorizing nonwoven fabric layer measured by Frajour type method is in the range from 60 to 350 cm$^3$/(cm$^2$·s), and said dust-proof nonwoven fabric layer has an air permeability equal to or smaller than 146/246 of an air permeability of said deodorizing nonwoven fabric layer.

\* \* \* \* \*